United States Patent [19]

Stevenson et al.

[11] Patent Number: 5,215,517
[45] Date of Patent: * Jun. 1, 1993

[54] FLAT CERVICAL COLLAR

[75] Inventors: Vernon L. Stevenson, Ft. Worth; Paul N. Brost, Colleyville, both of Tex.

[73] Assignee: Tecnol Medical Products, Inc., North Richland Hills, Tex.

[*] Notice: The portion of the term of this patent subsequent to Jan. 28, 2009 has been disclaimed.

[21] Appl. No.: 825,545

[22] Filed: Jan. 24, 1992

Related U.S. Application Data

[63] Continuation of Ser. No. 508,787, Apr. 12, 1990, Pat. No. 5,083,553.

[51] Int. Cl.⁵ .............................. A61F 5/08
[52] U.S. Cl. ................................ 602/18; 602/17; 128/DIG. 23
[58] Field of Search ................... 602/17, 18; 128/DIG. 23

[56] References Cited

U.S. PATENT DOCUMENTS

Re. 32,219  8/1986  Garth .
2,818,063  12/1957  Smith et al. .
3,042,027  7/1962  Monfardini .
3,306,284  2/1967  McKinley .
3,504,667  4/1970  McFarlane .
3,756,226  9/1973  Calabrese et al. .
3,916,885  11/1975  Gaylord, Jr. .
4,413,619  11/1983  Garth .
4,538,597  9/1985  Lerman .
4,712,540  12/1987  Tucker et al. .

Primary Examiner—Richard J. Apley
Assistant Examiner—Linda C. M. Dvorak
Attorney, Agent, or Firm—Baker & Botts

[57] ABSTRACT

A cervical collar arranged to be stored flat comprises an anterior member, a generally C-shaped chin support member, a connecting pin attaching each end of the chin support member to the anterior member, a posterior member formed to provide a back engaging edge portion and an occipital support portion, and fastening means for releasably retaining the ends of the anterior and posterior means in juxtaposition. Another cervical collar is similarly constructed, but has the chin support preformed and attached to the anterior member or formed as an integral part of the anterior member.

1 Claim, 3 Drawing Sheets

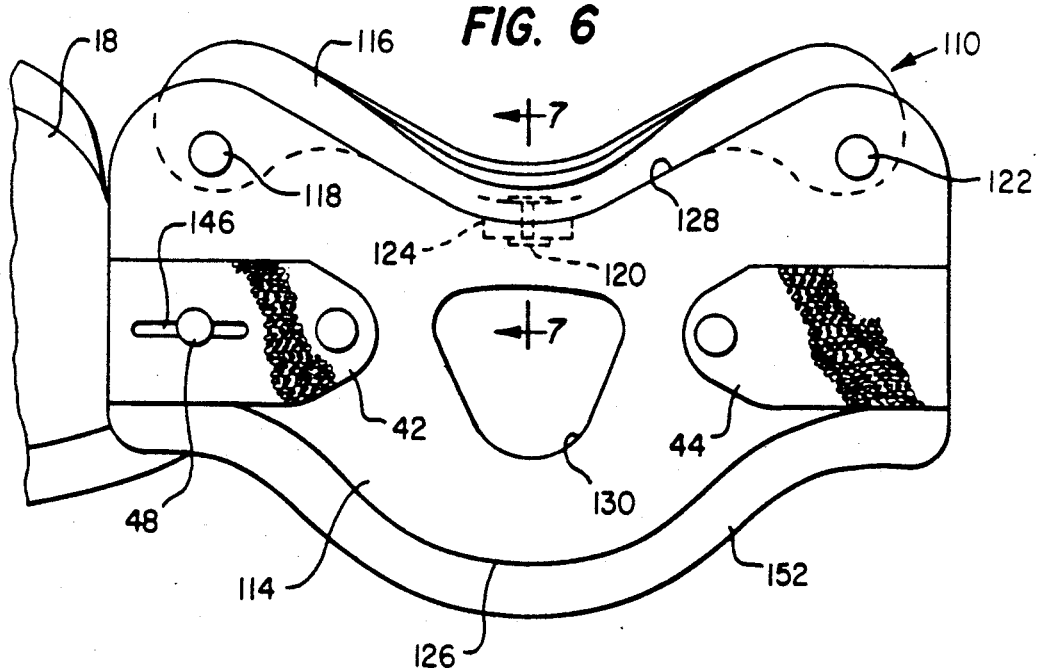
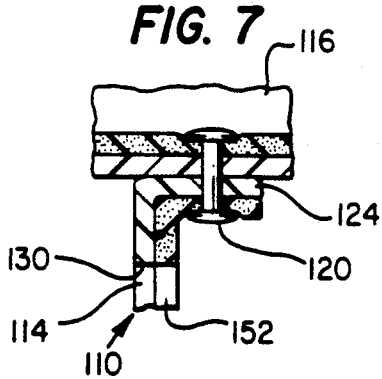
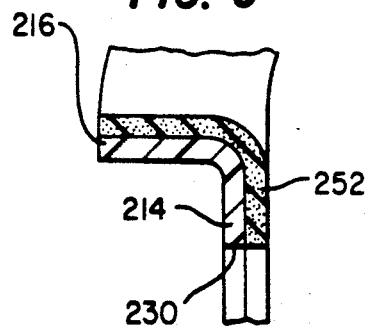
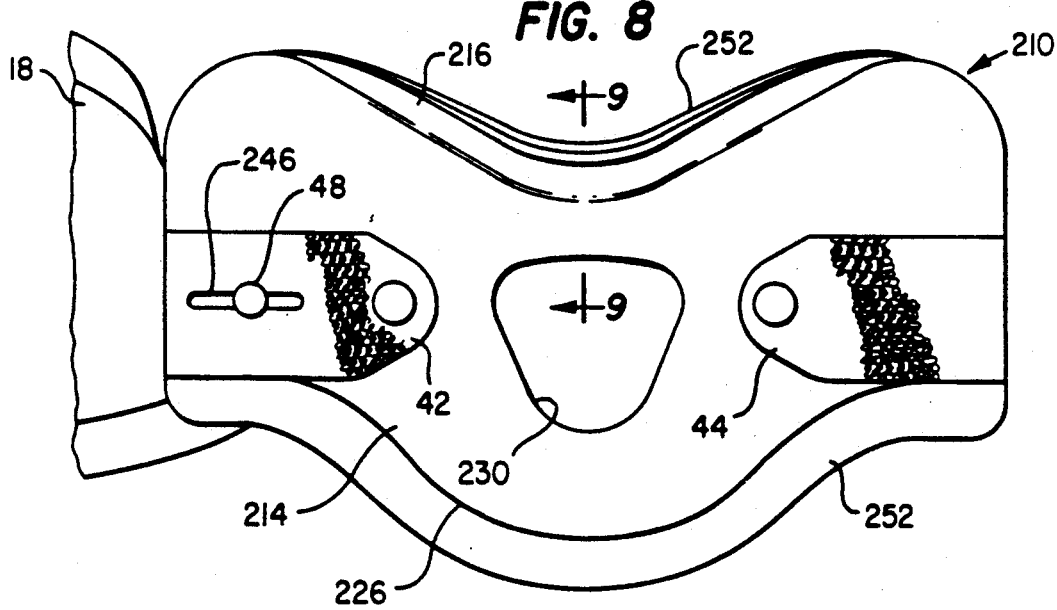

though designated by
FLAT CERVICAL COLLAR

RELATED APPLICATIONS

This application is a continuation of application Ser. No. 07/508,787, filed Apr. 12, 1990 and entitled "Cervical Collar", now U.S. Pat. No. 5,083,553, issued Jan. 28, 1992.

TECHNICAL FIELD OF THE INVENTION

This invention relates generally to an orthopedic device for supporting the neck and head of the wearer. More particularly, but not by way of limitation, this invention relates to an improved cervical collar that can be stored flat or substantially flat and when assembled, provides 360 degree support for the neck and head of the wearer.

BACKGROUND OF THE INVENTION

Over the years, cervical collars that are capable of being stored flat have generally been constructed from a one piece, relatively heavy strap formed from material such as leather or heavy plastic that included metal braces of one type or another. Such collars are illustrated in U.S. Pat. No. 2,818,063 issued Dec. 31, 1957 to T. W. Smith et al.; U.S. Pat. No. 3,042,027 issued Jul. 3, 1962 to L. P. Monfardini; and U.S. Pat. No. 3,504,667 issued Apr. 7, 1970 to A. J. McFarlane. The described collars were reasonably successful in immobilizing the head in one or more directions. However, the presence of the metal stays made X-ray of the neck area impossible without removal of the collar. None of the collars provided tracheotomy holes and all were heavy, cumbersome, and expensive.

More recently, and with the advent of better plastic materials, cervical collars are now generally constructed from relatively stiff or rigid plastic materials that are capable of being bent along a long axis to encircle the neck of the wearer and yet, along their smaller axis, provide substantial support to the head of the wearer. Also, such collars are frequently lined with a softer plastic material for the comfort of the wearer. Such collars are illustrated in U.S. Pat. No. 3,756,226 issued Sep. 4, 1973 to Calabrese et al. and U.S. Pat. No. Re. 32,219 reissued Aug. 5, 1986 to Geoffrey C. Garth.

The Garth patent in particular, illustrates a cervical collar suitable for use in emergency situations and one that can be stored flat. The collar illustrated therein includes a relatively rigid plastic frame or body that has a certain amount of softer plastic lining material attached to the body for the comfort of the wearer. It also includes a flat chin support member which is deformed to provide a chin support for the wearer. It is noted that the body of the collar is asymmetrical and made to form a one piece strap that can be slipped behind the neck of the wearer. The front portion of the strap is then shaped by attaching a loose end of the chin support member in the proper position which deforms the strap. The strap is then in position around the neck of the wearer so that fastening means between the ends of the one piece member can be connected to complete the formation of the cervical collar.

While the collar can be formed or stored in a flat position, it will be noted that the one piece asymmetrical construction of the strap is relatively long and makes the storing of the collar difficult.

SUMMARY OF THE INVENTION

An object of this invention is to provide an improved cervical collar that is constructed from a plurality of symmetrical members that provide occipital support, lateral support, and forward support for the head of the wearer of the collar. Components of the collar are capable of being pivoted or otherwise moved relative to the remaining parts so that the apparatus can be folded into a rather compact package that can be stored flat in a relatively small space. The collar is, because of this, very useful to paramedics, firemen, and the like.

In one aspect, this invention provides a cervical collar arranged to be stored flat that comprises: an elongated anterior member formed from a stiff, flexible plastic sheet; a generally C-shaped chin support member formed from a stiff, flexible plastic sheet; and a posterior member formed from a stiff, flexible plastic sheet. The chin support member is connected to the anterior member by a pair of pins located in mating slots in the anterior member which permit the members to be flattened when not assembled into a cervical collar. Fasteners are provided which join the ends of the anterior and posterior members when the collar is placed around the neck of the wearer.

In another aspect, this invention provides a cervical collar arranged to be stored substantially flat that includes posterior and anterior members and a chin support member that is preformed and mounted on the anterior member or that is formed as a part of the anterior member.

BRIEF DESCRIPTION OF THE DRAWING

The foregoing and additional objects and advantages of the invention will become more apparent as the following detailed description is read in conjunction with the accompanying drawing wherein like reference characters denote like parts in all views and wherein:

FIG. 6 is a layout view of another embodiment of the collar that is also constructed in accordance with the invention.

FIG. 7 is a fragmentary cross-sectional view taken generally along the line 7—7 of FIG. 6.

FIG. 8 is a layout view of another embodiment of the collar that is also constructed in accordance with the invention.

FIG. 9 is a fragmentary cross-sectional view taken generally along the line 9—9 of FIG. 8.

DETAILED DESCRIPTION OF THE PREFERRED EMBODIMENT

Figure 1:
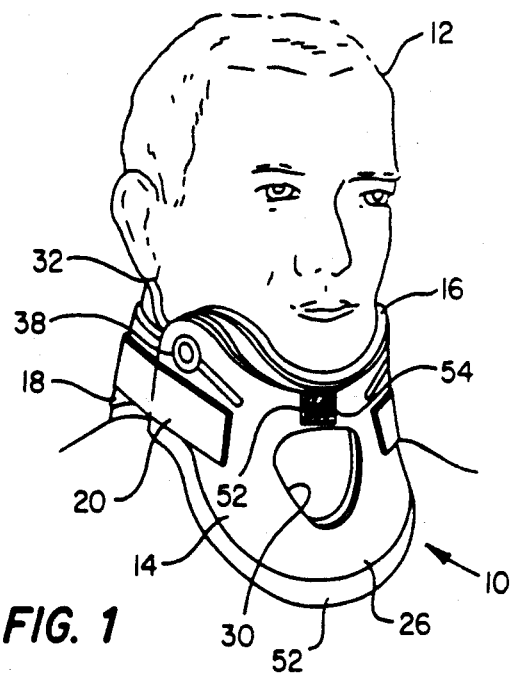
FIG. 1 is a front view of an assembled cervical collar that is constructed in accordance with the invention installed on the neck of a wearer.
Figure 2:
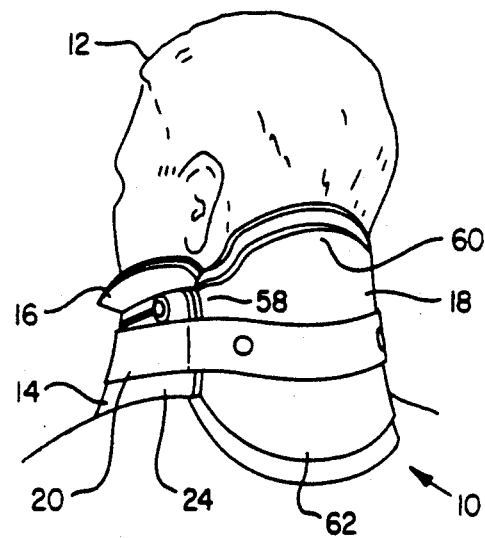
FIG. 2 is a rear view of the assembled cervical collar of FIG. 1.

Referring to the drawing and to FIGS. 1 and 2 in particular, shown therein and generally designated by the reference character 10 is a cervical collar that is constructed in accordance with the invention located on a wearer 12 shown in phantom lines. The cervical collar 10 includes an anterior member 14, a chin support member 16, and a posterior member 18. Fastening means 20 such as a VELCRO, also known as hook and loop material, strap is utilized to connect the anterior and posterior members 14 and 18, respectively, around the neck of the wearer 12.

It will be noted in FIGS. 1 and 2 that the anterior member 14 is symmetrical about a vertical centerline and engages the breast of the wearer 12 and through the chin support member 16 prevents forward movement of the head of the wearer. The posterior member 18, which is also symmetrical about a vertical centerline, engages the back of the wearer 12 as well as the occipital area preventing movement of the head of the wearer to the rear. The anterior and posterior members 14 and 18 overlap under the fastening means 20 and are retained in relatively tight engagement with the wearer's neck and head to prevent lateral movement of the head. Thus, the collar 10 provides 360 degree support for the head and neck of the wearer 12.

Figure 3:
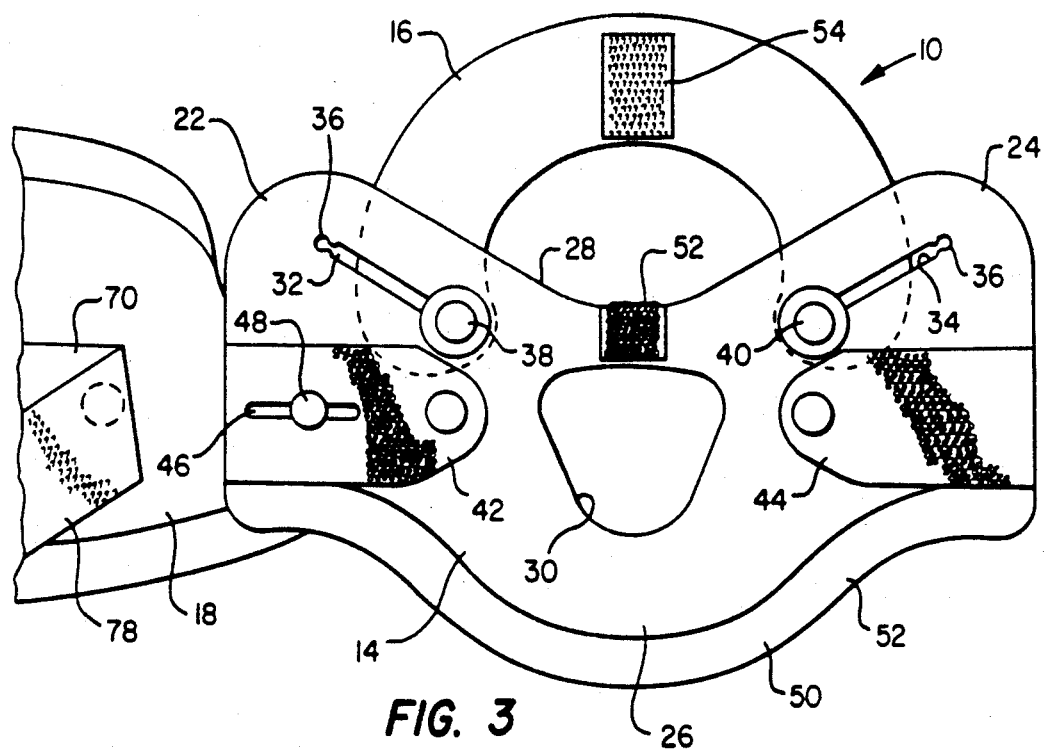
FIG. 3 is a layout view of the anterior member and chin support member of the cervical collar of FIG. 1 which is constructed in accordance with the invention.

In FIG. 3, the collar 10 is laid out flat prior to shaping the collar 10 around the neck of the wearer as illustrated in FIGS. 1 and 2. As shown in FIG. 3, the anterior member 14 includes first and second end portions 22 and 24, a breast engaging portion 26 that is convex in configuration and a concave edge portion 28 that will support the chin support member 16 as will be described hereinafter.

The anterior portion 14 also includes a tracheotomy hole 30 that extends therethrough. The tracheotomy hole 30 is positioned adjacent the trachea of the wearer 12 and is provided to permit ease of access to the trachea when the collar 10 is in place on the wearer 12.

Diagonally extending slots 32 and 34 are located adjacent the end portions 22 and 24 of the anterior member 14. Abutments 36 are located adjacent the outer ends of the slots 32 and 34 and extend slightly into the slots. Fastening pins 38 and 40 adjustably connect the chin support member 16 to the anterior member 14. The pins 38 and 40 are movably located in the slots 32 and 34, respectively, and have a diameter large enough to engage the abutments 36.

VELCRO, also known as hook and loop material, fastening members 42 and 44 are located on the front surface of the anterior member 14. Extending through the fastening member 42 is a slot 46 which also extends through the anterior member 14 providing for the adjustable connection of the posterior member 18 to the end portion 22 of the anterior member 14. For this purpose, an adjusting pin 48 connected to posterior member 18 is located in the slot 46.

Although only the lower edge is visible, a soft, closed cell plastic lining 50 is attached to one surface of the anterior portion 14. A lower edge portion 51 of the lining 50 extends downwardly below the chest engaging portion 26 of the anterior member 14. The lining 50 is provided for the purpose of making the collar more comfortable to the wearer thereof.

Also located on the anterior member 14 is a patch of VELCRO, also known as hook and loop material, material 52 which extends over the edge 28 thereof.

The VELCRO, also known as hook and loop material, patch 52 is releasably engageable with a mating VELCRO, also known as hook and loop material, patch 54 carried by the chin support member 16. As may be seen in FIG. 1, the patches 52 and 54 are engaged to aid in retaining the chin support member 16 in the deformed or shaped configuration for engaging the chin of the wearer 12.

Although not shown, it will also be understood that one surface of the chin support member 16 is also coated with the soft, closed cell foam plastic as used in forming the lining 50.

Figure 4:
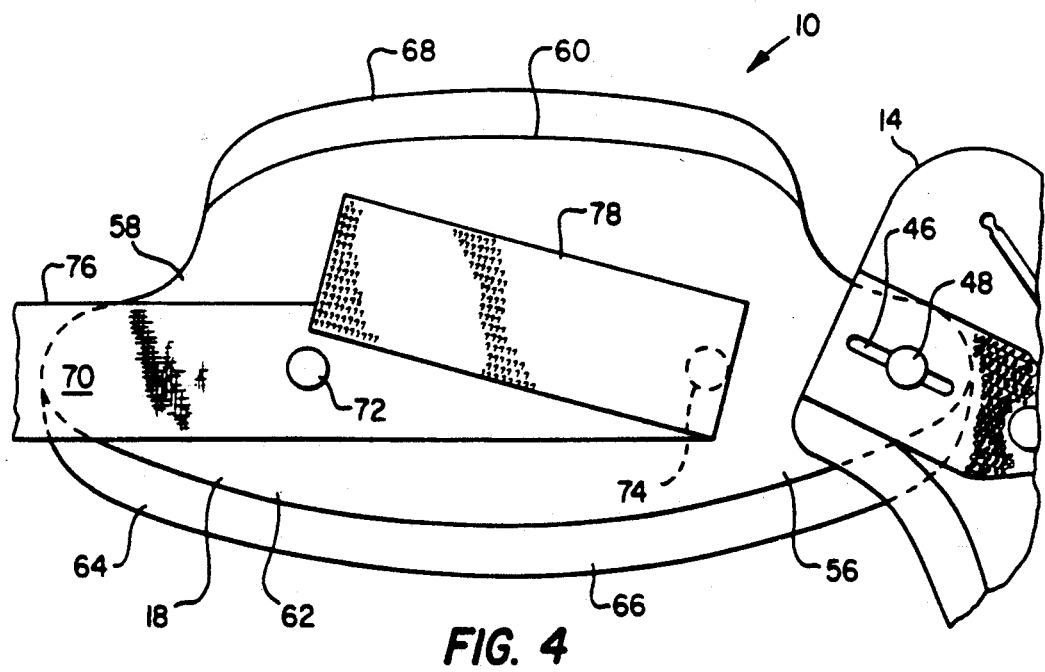
FIG. 4 is a layout view of a posterior member of the cervical collar of FIG. 1.

As shown most clearly in FIG. 4, the posterior member 18 is also composed of a relatively stiff plastic material that includes a first end portion 56 which is juxtaposed and adjustably interconnected with the anterior member 14 by the pin 48. The posterior member 18 and anterior member 14 do not need to be connected. The connection therebetween is a matter of convenience, primarily to prevent mixing of various sizes of collars that may be stored together.

A second end portion 58 on the posterior member 18 is arranged to be inserted between the second end portion 24 of the anterior member 14 and the wearer 12 as is illustrated in FIG. 2. The posterior member 18 also includes an occipital support edge portion 60 and a back engaging edge portion 62.

The posterior member 18 is also provided on one surface with a lining 64 that projects outwardly as shown at 66 below the back engaging edge portion 62 and projects outwardly from the occipital support edge portion 60 as shown at 68. Again, the lining 64 is provided for the purpose of increasing the comfort of the wearer of the cervical collar 10 and is constructed from the soft, close cell foam plastic.

To retain the cervical collar 10 assembled about the neck of the wearer 12, a strap 70, preferably of VELCRO material, is connected to the posterior member 18 by rivets 72 and 74. As can be seen in FIG. 4, the strap 70 includes an end 76 that projects beyond the second end portion 58 of the posterior member 18. A second end 78, although illustrated as being folded for purposes of clarity, also extends past the first end portion 56 of the posterior member 18. The patches 42 and 44, along with the strap 70, comprise the fastening means 20.

OPERATION OF THE PREFERRED EMBODIMENT

Figure 5:
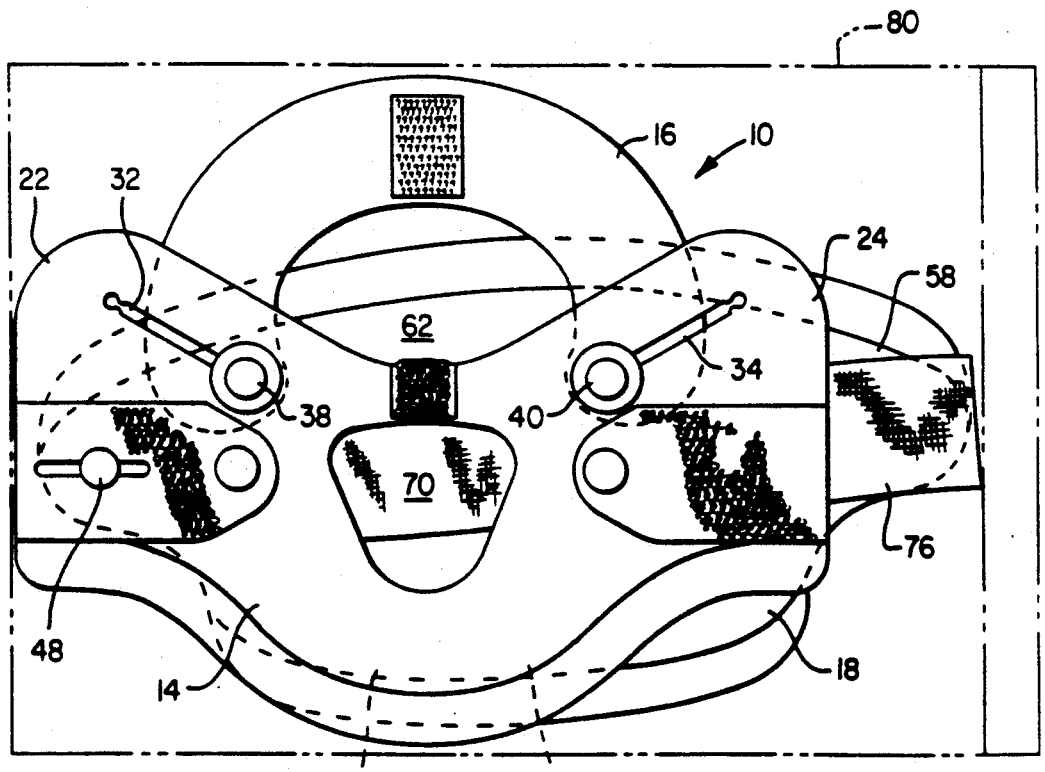
FIG. 5 is a view of the cervical collar of FIG. 1 arranged in a flat, folded storage condition and located in a storage bag.

As previously mentioned, one of the advantages of the cervical collar 10 is that it can be folded flat for storage and for reducing the space required for carrying the collars on emergency vehicles. FIG. 5 illustrates the condition of the certical collar 10 when located in a storage bag 80 shown in phantom lines on FIG. 5. It will be noted in FIG. 5 that the folded collar 10 is essentially symmetrical about a vertical centerline.

As shown therein, the pins 38 and 40 connecting the chin support member 16 with the anterior member 14 have been moved to the innermost ends of the slots 32 and 34. This permits the chin support member 16 and the anterior member 14 to be flattened.

After this has been accomplished, the posterior member 18 is rotated about the connecting pin 48 to a position directly behind the anterior member 14 and chin support member 16. This is the position of the parts of the collar 10 as illustrated in FIG. 5. It will be appreciated that in such condition the collar is very compact, forming a flat package which can be inserted into the storage bag 80.

When placing the cervical collar 10 on the wearer 12, the cervical collar 10 is removed from the bag 80 and the posterior member 18 rotated about the pin 48 so that it is in a position approximately as illustrated in FIG. 3. The chin support member 16 is then grasped with one hand and the anterior member 14 with the other, pulling them relatively apart to move the pins 38 and 40 through the slots 32 and 34 and past the detents or abutments 36 so that the pins 38 and 40 are retained at the outermost ends of the slots 32 and 34. Since the distance between the pins 38 and 40 is substantially less than the distance between the outermost ends of the slots 32 and 34, the anterior member 14 is bowed slightly. The chin support member 16 is then pushed forward with the patch 54 being moved downwardly into engagement with the patch 52 located on the anterior member 14. With the patches thus engaged, the chin support member follows and is supported by the contour of the concave edge portion 28. The anterior portion 14 and chin support member 16 are substantially in the position illustrated in FIGS. 1 and 2.

The posterior member 18 is then placed behind the neck of the wearer 12. Pulling on the end 76 of the strap 70 deforms the posterior member 18 into the configuration illustrated in FIGS. 1 and 2. At this time, adjustment can be made by the pin 48 and slot 46 arrangement to position the chin support member 16 accurately with respect to the user's chin and at the same time placing the occipital support edge portion 60 at the proper location at the back of the head.

Once the adjustment has been made, the end 78 of the strap 70 is brought into engagement with the patch 42 locking the anterior member 14 and the posterior member 18 against further relative movement. To complete the application of the cervical collar to the user 12, the end portion 58 of the posterior member 18 is brought into juxtaposition with the inside of the end portion 24 of the anterior member 14 and the end 76 of the strap 70 is brought into holding engagement with the patch 44 located on the anterior member 14.

It should be pointed out that in the preferred form of construction of the cervical collar 10, there are no metal parts utilized with all the pins and rivets being constructed from plastic so that an X-ray of the neck area can be made without interference from the cervical collar 10.

From the foregoing comments it should be apparent that the embodiment of cervical collar described in detail hereinbefore is one that is capable of providing 360 degree support to the wearer thereof while at the same time being capable of being folded flat for storage so that it can be conveniently carried by paramedics and the like.

THE EMBODIMENT OF FIG. 6

FIGS. 6 and 7 illustrate another embodiment of a cervical collar that is also constructed in accordance with the invention and that is generally designated by the reference character 110. The cervical collar 110 includes the posterior member 18 constructed as previously described in connection with the cervical collar 10.

The cervical collar 110 also includes an anterior member 114 and a chin support member 116 affixed to the anterior member 114 by rivets 118, 120 and 122. As may be seen more clearly in the fragmentary cross-sectional view of FIG. 7, the rivet 120 extends through the chin support member 116 and through a tab 124 that is formed on an upper convex edge 128 of the anterior member 114.

The anterior member 114 also includes a breast engaging lower convex edge portion 126. Extending below the edge portion 126 is a soft plastic foam member 152 which is the liner for the anterior member 114.

The posterior member 18 is pivotally and adjustably connected to the anterior member 114. Pivotal movement is provided by an adjusting pin 48 that extends through a slot 146 formed in the anterior member 114. The slot 146 permits longitudinal adjustment of the anterior and posterior members 114 and 18 and relative to each other.

VELCRO, also known as hook and loop material, pads or patches 42 and 44 are illustrated as being attached to the front surface of the anterior member 114. The patches 42 and 44 function in conjunction with the VELCRO, also known as hook and loop material, strap 70 which is mounted on the posterior member 18 (see FIGS. 3 and 4). The strap 70 and the patches 42 and 44 are utilized to retain the collar 114 in the assembled position about the neck of a wearer of the cervical collar 110.

The anterior member 114 also has a tracheotomy hole 130 extending therethrough. The hole 130 is positioned so that it is located in the appropriate position on the wearer in the event that a tracheotomy needs to be performed.

FIG. 7 illustrates that the preformed chin support member 116 has a thickness so that the cervical collar 110 cannot be folded completely flat as the cervical collar 10. However, when the posterior member 18 is pivoted about the pivot pin 48 to a position behind the anterior member 114 for storage as illustrated for the cervical collar 10 in FIG. 5, only a slightly greater depth is required for storage of the cervical collar 110 that includes the preformed chin support member 116.

THE EMBODIMENT OF FIG. 8

FIGS. 8 and 9 illustrate another embodiment of a cervical collar that is constructed in accordance with the invention and generally designated by the reference character 210. As illustrated therein, the cervical collar 210 includes the posterior member 18 which is constructed as previously described in connection with the cervical collar 10.

The cervical collar 210 also includes an anterior member 214 that has a chin support portion 216 formed integrally therewith. The chin support portion 216 projects at a substantially right angle relative to said anterior member 214. The anterior member 214 also includes a lower convex edge portion 226 that is arranged to engage the breast of the wearer of the collar 210. A soft plastic foam liner 252 can be seen extending below the edge 226 and above the chin support portion 216. Preferably, the chin support portion 216 is molded as a portion of the anterior member 214.

In addition to the chin support portion 216, VELCRO, also known as hook and loop material, VELCRO fastener pads or patches 42 and 44 are secured to the front of the anterior member 214. The patches 42 and 44 function in conjunction with the VELCRO, also known as hook and loop material, straps 70 mounted on the posterior member 18 as described in connection with the cervical collar 10. The posterior member 18 is pivotally and adjustably connected to the anterior member 214 by a pivot pin 48 that extends through a slot 246 formed in the anterior member 214.

A tracheotomy hole 230 extends through the anterior member 214. The hole 230 is positioned so that when the collar 210 is mounted on a wearer, the hole 230 is located in the appropriate position for performing a tracheotomy on the wearer if needed.

As is evident from viewing FIG. 9, the collar 210 has a depth somewhat greater than that of the collar 10 when in the storage position. However, the difference in thickness is only that distance that the chin support portion 216 protrudes forwardly from the surface of the anterior member 214.

With regard to the collars 110 and 210, it will of course be understood that in the design of those collars, the particular arrangement of the chin support member 116 and the chin support portion 216 is such that upon bending of the anterior member 114 to partially encircle the neck of the wearer, the chin support member or chin support portion will be configured to receive the chin of the wearer.

Also, with respect to the collars 110 and 210, it will be appreciated that each is capable of being stored in a manner similar to the storage of the collar 10 as illustrated in FIG. 5. A little less width will be required in the packaging since the chin support member or portion does not extend outwardly as far as the chin support member 16 of the collar 10. However, and as previously pointed out, additional depth is required in the packaging due to the forward projection of the chin support member 116 and of the chin support portion 216.

The embodiments described hereinbefore are presented by way of example and it will be understood that many changes and modifications can be made thereto without departing from the spirit or scope of the invention.

What is claimed is:

1. A cervical collar arranged to be stored flat comprising:

a flat, elongated anterior member formed from a stiff, flexible plastic sheet, said anterior member including first and second ends, a convex breast engaging edge portion, and a concave edge portion;

a chin support member formed from a stiff, flexible plastic sheet, said chin support member being connected to said anterior member adjacent to said concave edge portion;

slidable connecting means joining said chin support member and anterior member and adaptable for adjusting said chin support member to lie flat in the same plane as said flat anterior member;

a flat posterior member formed from a stiff, flexible plastic sheet including first and second ends and including a back engaging portion and an occipital support portion;

fastening means for releasably retaining the ends of said anterior and posterior members in juxtaposition; and wherein said anterior member, posterior member, and chin support portion include, respectively, an anterior, posterior, and chin support lining member affixed thereto that are constructed from soft, closed cell foam plastic material.

* * * * *